United States Patent [19]
Hammons et al.

[11] Patent Number: 5,558,657
[45] Date of Patent: Sep. 24, 1996

[54] ABSORBENT ARTICLES HAVING OVERLAPPING UNDERGARMENT COVERING COMPONENTS THAT AUTOMATICALLY WRAP THE SIDES OF UNDERGARMENTS

[75] Inventors: John L. Hammons, Hamilton; Patricia L. Lampson; Thomas W. Osborn, III, both of Cincinnati, all of Ohio

[73] Assignee: The Procter & Gamble Company, Cincinnati, Ohio

[21] Appl. No.: 276,070

[22] Filed: Jul. 15, 1994

Related U.S. Application Data

[63] Continuation-in-part of Ser. No. 915,133, Jul. 23, 1992, abandoned, Ser. No. 42,840, Apr. 5, 1993, Pat. No. 5,354,400, Ser. No. 73,256, Jun. 4, 1993, Pat. No. 5,389,094, Ser. No. 96,121, Jul. 22, 1993, Ser. No. 109,017, Aug. 18, 1993, Pat. No. 5,344,416, Ser. No. 192,240, Feb. 4, 1994.

[51] Int. Cl.⁶ ..................................................... A61F 13/16
[52] U.S. Cl. .......................................... 604/385.1; 604/387
[58] Field of Search ............................. 604/358, 385.1, 604/386, 387

[56] References Cited

U.S. PATENT DOCUMENTS

| | | |
|---|---|---|
| 2,787,271 | 4/1957 | Clark . |
| 3,397,697 | 8/1968 | Rickard . |
| 4,166,464 | 9/1979 | Korpman . |
| 4,285,343 | 8/1981 | McNair . |
| 4,589,876 | 5/1986 | Van Tilburg . |
| 4,608,047 | 8/1986 | Mattingly . |
| 4,687,478 | 8/1987 | Van Tilburg . |
| 4,900,320 | 2/1990 | McCoy . |
| 4,911,701 | 3/1990 | Mavinkurve . |
| 4,917,697 | 4/1990 | Osborn et al. . |
| 4,940,462 | 7/1990 | Salerno . |
| 4,950,264 | 8/1990 | Osborn . |
| 5,007,906 | 4/1991 | Osborn et al. . |
| 5,009,653 | 4/1991 | Osborn . |
| 5,125,918 | 6/1992 | Seidy . |
| 5,281,209 | 1/1994 | Osborn et al. . |
| 5,324,278 | 7/1994 | Visscher et al. . |
| 5,346,486 | 9/1994 | Osborn et al. . |
| 5,389,094 | 2/1995 | Lavash et al. ................ 604/385.2 |
| 5,401,268 | 3/1995 | Rodier ........................... 604/385.1 |

FOREIGN PATENT DOCUMENTS

| | | |
|---|---|---|
| 0426235A2 | 5/1991 | European Pat. Off. . |
| 0446818A2 | 9/1991 | European Pat. Off. . |
| 0467184A1 | 1/1992 | European Pat. Off. . |
| 0511905A1 | 11/1992 | European Pat. Off. . |
| 0539032A1 | 4/1993 | European Pat. Off. . |
| 40-36391 | 12/1965 | Japan . |
| 236101 | 10/1993 | New Zealand . |
| 2168253 | 6/1986 | United Kingdom . |
| WO92/07535 | 5/1992 | WIPO . |
| WO93/01785 | 2/1993 | WIPO . |
| WO93/01786 | 2/1993 | WIPO . |
| WO93/06805 | 4/1993 | WIPO . |

*Primary Examiner*—David H. Willse
*Assistant Examiner*—Mark O. Polutta
*Attorney, Agent, or Firm*—Jeffrey V. Bamber; Steven W. Miller; E. Kelly Linman

[57] ABSTRACT

The present invention relates to absorbent articles such as sanitary napkins, panty liners, and incontinence pads. More particularly, the present invention relates to absorbent articles, such as sanitary napkins, that have longitudinal side wrapping elements comprising overlapping components that automatically wrap the sides of a wearer's panties and provide an alternative to conventional side flaps.

8 Claims, 3 Drawing Sheets ation-in-part of the following U.S. patent
ABSORBENT ARTICLES HAVING OVERLAPPING UNDERGARMENT COVERING COMPONENTS THAT AUTOMATICALLY WRAP THE SIDES OF UNDERGARMENTS

CROSS-REFERENCE TO RELATED APPLICATIONS

This is a continuation-in-part of the following U.S. patent applications: Ser. No. 07/915,133 filed Jul. 23, 1992 now abandoned; Ser. No. 08/042,840 filed Apr. 5, 1993 now U.S. Pat. No. 5,354,400; Ser. No. 08/073,256 filed Jun. 4, 1993 now U.S. Pat. No. 5,389,094; Ser. No. 08/096,121 filed Jul. 22, 1993; Ser. No. 08/109,017 filed Aug. 18, 1993 now U.S. Pat. No. 5,344,416; Ser. No. 08/124,180 filed Sep. 17, 1993; and Ser. No. 08/192,240 filed Feb. 4, 1994.

FIELD OF THE INVENTION

The present invention relates to absorbent articles such as sanitary napkins, panty liners, and incontinence pads. More particularly, the present invention relates to sanitary napkins that have undergarment covering components (or "side wrapping elements") comprising overlapping components. The side wrapping elements automatically wrap the sides of a wearer's undergarments when the undergarments are pulled up to provide an alternative to conventional side flaps.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body. Sanitary napkins both with and without side flaps (or wings) are disclosed in the literature and are available in the marketplace.

Generally when sanitary napkins are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are particularly effective for preventing exudates from soiling the edges of the wearer's panties.

Sanitary napkins having flaps of various types are disclosed in U.S. Pat. No. 4,687,478, entitled "Shaped Sanitary Napkin With Flaps", which issued to Van Tilburg on Aug. 18, 1987; U.S. Pat. No. 4,608,047, entitled "Sanitary Napkin Attachment Means", which issued to Mattingly on Aug. 26, 1986; U.S. Pat. No. 4,589,876, entitled "Sanitary Napkin", which issued to Van Tilburg on May 20, 1986 and its Reexamination U.S. Pat. No. B 4,589,876, Certificate of Reexamination issued Apr. 27, 1993; U.S. Pat. No. 4,285,343, entitled "Sanitary Napkin", which issued to McNair on Aug. 25, 1981; U.S. Pat. No. 3,397,697, entitled "Disposable Sanitary Shield For Undergarments", which issued to Rickard on Aug. 20, 1968; and, U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, some women find applying sanitary napkins having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. As a result, some women still prefer a sanitary napkin without flaps. In addition, some women who generally prefer a sanitary napkin with flaps, occasionally (such as during periods of light flow) prefer a sanitary napkin without flaps. Therefore, there is a need for a sanitary napkin which provides an alternative to sanitary napkins having conventional side flaps while still providing the protection of side flaps.

Several variations of sanitary napkins having conventional flaps that attempt to solve some, but not all of these problems are disclosed in the patent literature. For example, U.S. Pat. No. 4,911,701 issued to Mavinkurve discloses a sanitary napkin having elastic strands for providing a greater convex shape to the body-facing portion of the central absorbent and for enabling adhesive-free placement of the flaps of a winged napkin embodiment into a pair of panties. The sanitary napkin described in the Mavinkurve patent, however, still appears to require the user to manipulate the flaps (by first flipping the flaps upward and then placing the flaps in her panties and flipping the flaps back down) since the flaps appear to be pre-disposed to be in a downward folded condition. The Mavinkurve patent also requires that individual elastic strands be attached in a contracted condition to the central absorbent portion of the napkin and/or to its wings or flaps. The napkins described in the Mavinkurve patent can, therefore, be difficult and expensive to manufacture. U.S. Pat. No. 4,940,462 issued to Salerno discloses a sanitary napkin with longitudinally expandable flaps. The flaps are designed to fold over the exterior of the wearer's panty and then to expand to conform with the contour of the panties. The Salerno patent, however, appears to require conventional adhesive fasteners to retain the flaps in place on the underside of the wearer's panties.

Thus, a need exists for an absorbent article, such as a sanitary napkin, that is provided with an alternative to conventional flaps. In particular, a need exists for a sanitary napkin having an alternative to conventional flaps which provides the protection from soiling of conventional flaps and which can conveniently and efficiently solve the problems caused when attempting to attach conventional flaps to the underside of the wearer's panties.

It is, therefore, an object of the present invention to provide an absorbent article, such as a sanitary napkin, that is able to provide coverage to the wearer's panties to reduce side soiling (i.e., staining of the edges of the panty crotch) without the use of conventional flaps.

It is another object of the present invention to provide an absorbent article, such as a sanitary napkin that automatically wraps around the sides of the wearer's panties by the simple action of the wearer pulling up her panties.

It is still another object of the present invention to provide an absorbent article, such as a sanitary napkin, that is able to wrap around the sides of the wearer's panties and stay without providing flaps having panty fasteners thereon, and without attaching separate elastic strands to the sanitary napkin.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has side wrapping elements that automatically wrap the sides of a wearer's undergarments when the undergarments are pulled up. The side wrapping elements provide an alternative to conventional side flaps.

The sanitary napkin has a longitudinal dimension extending in a longitudinal direction and a transverse dimension extending in a transverse direction. The sanitary napkin comprises a main body portion and a pair of side wrapping elements. The main body portion comprises an absorbent core, and has a body-facing side, a garment-facing side, and a pair of longitudinal side edges. The side wrapping elements are joined to the main body portion and extend laterally outward beyond the longitudinal side edges of the main body portion to distal edges. At least one of the side wrapping elements comprises more than one side wrapping element component. The side wrapping element components are flexible, and at least partially overlap. The side wrapping components are arranged so that they are free to move relative to each other in the longitudinal direction.

The sanitary napkin of the present invention provides an alternative to sanitary napkins having conventional side flaps for several reasons. The side wrapping elements do not extend far enough outward beyond the side edges of the wearer's panties to cause any inconvenience to the wearer. The side wrapping elements require no action on the part of the wearer in order to fold the side wrapping elements under their panties or to attach the same to their panties. The side wrapping elements, therefore, stay in place well enough to cover the sides edges of the wearer's panties without affixing them underneath the wearer's panties.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

1. General Characteristics of the Absorbent Article

Figure 1:
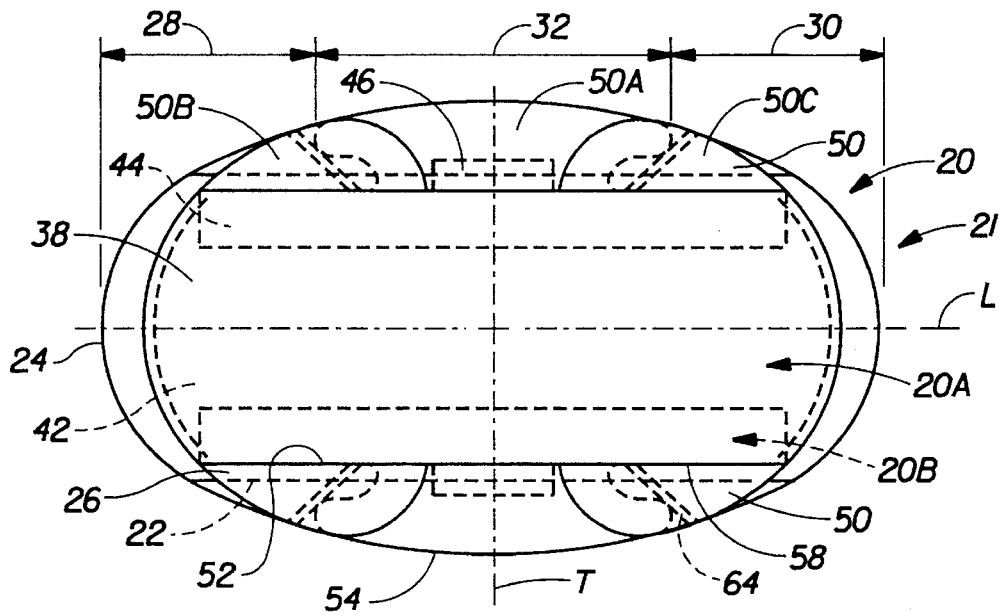
FIG. 1 is a top plan view of the sanitary napkin of the present invention.
Figure 2:
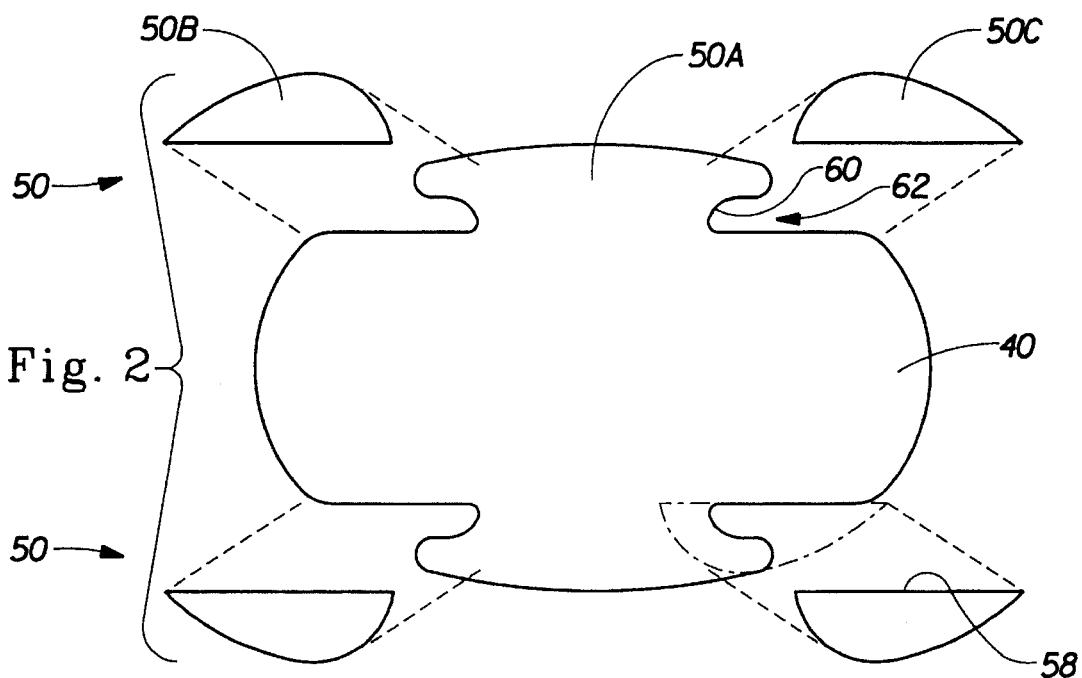
FIG. 2 is an exploded plan view showing the assembly of the components of the overlapping side wrapping elements of the sanitary napkin shown in FIG. 1.
Figure 3:
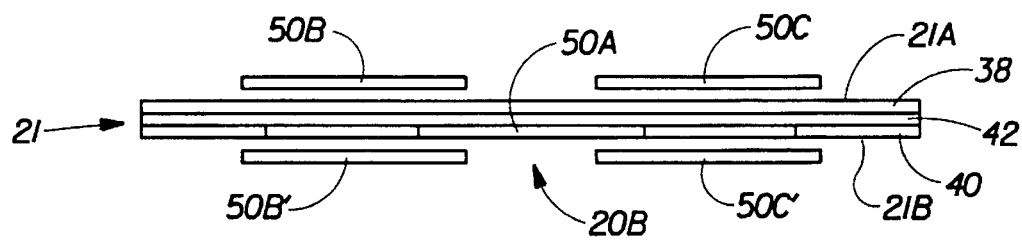
FIG. 3 is a schematic side view showing the assembly of the components of the sanitary napkin shown in FIG. 1.

FIGS. 1–3 show one preferred embodiment of a disposable absorbent article of the present invention, sanitary napkin 20. More particularly, the present invention relates to sanitary napkins that have a main body portion 21 and a pair of side wrapping elements 50 that automatically wrap the sides of the wearer's panties when the wearer places the sanitary napkin in her panties and pulls her panties up. The present invention, however, is not limited to absorbent articles having the specific configurations shown in the drawings.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 21 of the sanitary napkin 20 comprises the portion of the sanitary napkin without the side wrapping elements. The main body portion 21 has two spaced apart longitudinal edges 22, two spaced apart transverse or end edges (or "ends") 24, which together form the periphery 26 of the main body portion of the sanitary napkin 20. The main body portion also has two end regions, which are designated first end region 28 and second end region 30. A central region 32 is disposed between the end regions 28 and 30. The end regions 28 and 30 extend outwardly from the edges of the central region 32 about ⅛ to about ⅓ of the length of the main body portion. A detailed description of the central region 32 and the two end regions 28 and 30 is contained in U.S. Pat. No. 4,690,680 issued to Higgins on Sep. 1, 1987.

The main body portion 21 of the sanitary napkin 20 can be of any thickness, including relatively thick, relatively thin, or even very thin. The embodiment of the sanitary napkin 20 shown in FIGS. 1-3 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 as described in U.S. Pat. Nos. 4,950,264 and 5,009,653 issued to Osborn preferably has a caliper of less than about 3 millimeters. The sanitary napkin 20 shown preferably should also be relatively flexible, so that it is comfortable for the wearer.

FIG. 3 shows the individual components of the main body portion 21 of the sanitary napkin 20 of the present invention. The main body portion 21 shown in FIG. 3 generally comprises at least three primary components. These include a liquid pervious topsheet 38, a liquid impervious backsheet 40, and an absorbent core 42 positioned between the topsheet 38 and the backsheet 40. There are occasions, however, when one or more of these components, such as the backsheet, can be replaced by a component that serves as part of the side wrapping elements described herein. The topsheet, the backsheet, and the absorbent core may be assembled in a variety of configurations known in the art (including so called "sandwich" products and "tube" products).

Several preferred sanitary napkin configurations are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. No. 4,950,264, "Thin, Flexible Sanitary Napkin" issued to Osborn on Aug. 21, 1990; U.S. Pat. No. 5,308,346, "Elasticized Sanitary Napkin" issued to Sneller, et al. on May 3, 1994; U.S. patent application Ser. No. 08/096,121 entitled "Absorbent Articles Having Panty Covering Components That Naturally Wrap the Sides of Panties" filed Jul. 22, 1993, in the name of Lavash, et al.; and U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. The main body portion 21 of the sanitary napkin may also be comprised of one or more extensible components such as those sanitary napkins, and the like described in U.S. patent application Ser. Nos. 07/915,133 and 07/915,284 both filed Jul. 23, 1992, in the name of Osborn, et al. (PCT Publication Nos. WO 93/01785 and 93/01786, both published Feb. 4, 1993).

FIG. 1 shows a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to thereby form portions of the periphery 26. The sanitary napkin 20 of the present invention comprises pair of side wrapping elements 50 joined to the main body portion 21 that extend laterally outward beyond the longitudinal side edges 22 of the main body portion 21 from proximal edges 52 to their distal edges 54.

The side wrapping elements 50 can be of any suitable size and shape. The side wrapping elements 50 can have a length (longitudinal dimension) that varies within a large range. The length of the side wrapping elements 50 is preferably at least as large as the longitudinal dimension of known types of flaps that attach to each other or to the underside of a wearer's panties. The side wrapping elements 50, therefore, can primarily extend only from the central region 32 of the main body portion of the sanitary napkin. Alternatively, the side wrapping elements 50 can have a length that is as long as, or longer than, the length of the main body portion 21. The distal edges 54 of the side wrapping elements preferably extend outward beyond the longitudinal side edges 22 of the main body portion 21, a distance of less than one-half the width of the main body portion. The side wrapping elements 50 of the present invention preferably have the dimensions set forth for the panty covering components in the aforementioned U.S. patent application Ser. Nos. 08/096,121 and 08/124,180 filed in the names of Lavash, et al. and Mansfield, et al., which are incorporated by reference herein.

The side wrapping elements 50 can be joined to the main body portion 21 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Figure 4:
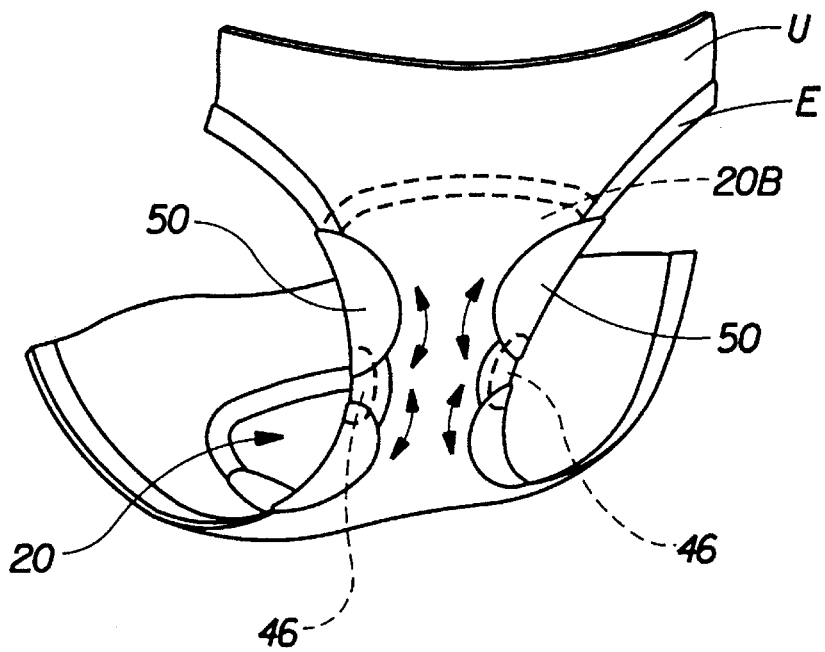
FIG. 4 is a perspective view showing the wrapping of the side wrapping elements around the side of a panty.

FIGS. 1–3, show that the side wrapping elements 50 comprise a plurality of overlapping side wrapping element components 50A, 50B, and 50C. The side wrapping element components 50A, 50B, and 50C are arranged so that they are free to move relative to each other (or spread out) in the longitudinal direction when they are folded around the crotch region of a pair of panties as shown in FIG. 4.

The side wrapping elements are assembled as shown in FIGS. 2 and 3. FIG. 2 shows that the side wrapping element components each comprise a central component 50A and a pair of end components 50B and 50C. Preferably, as shown in FIG. 2, the central components 50A comprise extensions of one or more components of the main body portion of the sanitary napkin, such as the backsheet 40. The end components 50B and 50C comprise separate pieces that are joined to the main body portion 21 of the sanitary napkin in an overlapping relationship with the central components 50A. In addition, as shown in FIG. 3, the side wrapping elements 50 also comprise a set of end components 50B' and 50C' that are disposed to overlap the garment-facing side of the central components. Thus, in the embodiment shown in FIGS. 1–3, each side wrapping element 52 comprises a total of four end components, two on top of the central components 50A (which are shown in FIG. 2) and two (identical to those shown in FIG. 2) positioned beneath the central components 50A.

The sanitary napkin 20, as shown in FIG. 3, is preferably assembled by first assembling the components of the main body portion 21. The end components are then joined at their proximal edges 58 to the longitudinal side edges 22 of the main body portion 21. The upper and lower end components of each set of end components are preferably also joined to each other by liquid impervious seals 64 that are positioned outboard of the distal edges of the central components. The impervious seals 64 prevent bodily exudates from wicking in the capillary spaces that are created between the overlapping components of the side wrapping elements. It is especially desirable to prevent liquids from wicking back toward the longitudinal side edges 22 of the main body portion 21. Liquids will still tend to wick along the side of the liquid impervious seal closest to the transverse centerline T. Capillary suction, however, will make liquids tend to stay between the layers of the side wrapping elements rather than wicking out beyond the distal edges 54 of the side wrapping elements. If liquids wicked beyond the distal edges of the side wrapping elements, this could cause soiling of the wearer's undergarments and clothing, etc. The liquid impervious seals 64 can be formed by any suitable attachment mechanisms. Suitable attachment mechanisms include adhesives, and any other attachment mechanisms that are known in the art as being suitable for use on absorbent articles.

The components of the side wrapping elements can be made from any of the materials used in the construction of the main body portion 21 of the sanitary napkin. These materials can be absorbent if the components of the side wrapping elements are suitably sealed to prevent the outward wicking of exudates from the distal edges of the side wrapping elements. Preferably, however, the components of the side wrapping elements are substantially non-absorbent. The components of the side wrapping elements that form the garment-facing side of the side wrapping elements (e.g., the central component 50A and lower end components 50B' and 50C') should also preferably be liquid impervious. The materials comprising the components of the side wrapping elements may either be inextensible, or extensible. The overlapping configuration of the side wrapping element components, however, provides the advantage that the components of the side wrapping elements can spread apart to wrap around a panty crotch without being provided with extensibility.

In the preferred embodiment shown in FIGS. 1–3, the central components 50A comprise backsheet material. The end components 50B, 50C, 50B', and 50C' preferably comprise a laminate of the apertured formed film material used for the topsheet and the polyethylene film used for the backsheet. The laminate pieces 50B and 50C are attached to the body-facing side 21A of the main body portion 21 with the topsheet material facing upward. Laminate pieces 50B' and 50C' are attached to the garment-facing side 21B of the main body portion with the topsheet material facing downward, although the orientation of these components are merely one preferred execution, and are not mandatory design features. The laminate pieces are chosen to provide the desired amount of resistance to edge compression so that the side wrapping elements will fold, rather than crumple, when they are subjected to compression by the wearer's thighs.

The side wrapping elements preferably have a relatively high resistance to edge compression and good fold retention in order to automatically wrap the edges of the wearer's panties and stay in place around the wearer's panties.

The term "resistance to edge compression" refers to the measurement of how substantial the material that comprises the side wrapping elements is. Specifically, edge compression refers to the tendency of the side wrapping elements 50 to buckle when the side wrapping elements are extended to form a planar extension and forces are applied perpendicular to the plane of the side wrapping elements. This property is important because if the side wrapping elements are insubstantial, they will bunch up when forces are applied to the side wrapping elements by the wearer's panty elastics or by the wearer's thighs during wear. The side wrapping elements may, for example, have a resistance to edge compression of greater than or equal to the following amounts: about 5 grams, about 7 grams, about 10 grams, and about 15 grams.

The term "fold retention" refers to the ability of the side wrapping elements to stay in place after they have been folded around a panty crotch. The side wrapping elements may, for example, have a fold retention of less than or equal to the following amounts: about 100°, about 90°, about 45°, and about 20°.

The resistance to edge compression and fold retention of the side wrapping elements are measured according to the tests set forth in U.S. patent application Ser. Nos. 08/096,121 and 08/124,180 are incorporated by reference herein.

The garment surface 20B of the sanitary napkin 20 may include, and preferably does include, fasteners for attaching the sanitary napkin to the wearer's undergarments. FIG. 1 shows the central pad fastener 44 which is adapted to secure the main body portion 21 of the sanitary napkin to the crotch region of an undergarment. Fasteners comprising adhesives have been found to work well for this purpose, with pressure-sensitive adhesives being preferred. Before the sanitary napkin 20 is placed in use, if an adhesive fastener is used, the adhesive is typically covered with a removable cover strip or release liner in order to keep the adhesive from sticking to a surface other than the crotch portion of the panty prior to use. Suitable release liners are also described in the above-referenced U.S. Pat. No. 4,917,697.

FIG. 1 shows a preferred arrangement which utilizes a pair of spaced apart longitudinally-oriented strips or zones of adhesive that are centered about the longitudinal centerline L. Each of the longitudinally-oriented zones of adhesive has a central lateral extension 46. The central lateral extensions 46 serve to adhere the side wrapping elements 50 around the crotch portion of the wearer's undergarments during vigorous motions by the wearer (although such fasteners are generally not required under normal circumstances).

The sanitary napkin 20 of the present invention is used by removing any release liner and thereafter placing the sanitary napkin 20 in a panty so that the adhesive (or other fastener) 44 contacts the panty and maintains the sanitary napkin in position within the panty during use. The side wrapping elements 50 automatically wrap around the sides of the wearer's panties by the simple action of the wearer pulling up her panties. The operation of the side wrapping elements 50 is distinguishable in several respects from that of conventional side flaps. Placing a sanitary napkin having conventional flaps in a pair of panties and pulling up the panties will not consistently provide the automatic sustained wraparound feature of the present invention. There are several reasons for this. The conventional flaps are not formed from a plurality of overlapping components, so they will not conform as well to the panties. Conventional flaps are also not provided with resistance to edge compression and a high fold retention, so that in cases where conventional flaps do wrap around the panties, they will not consistently stay wrapped. In addition, conventionally-sized flaps will have excess flap material that hangs down underneath the panties during wear. This material can move around excessively underneath the panties. The side wrapping elements of the present invention, on the other hand, have a span that is ideally just wide enough to wrap around the elastic-containing edges of the panties, but no wider, avoiding the problems associated with excess flap material.

The function of the side wrapping elements 50 can be thought of conceptually as being analogous to separate overlapping side wrapping elements that are each connected to the main body portion at a single point about which they can pivot. The particular embodiment shown in FIGS. 1–3 creates a "pocket door"-like structure. Each of the side wrapping elements 50 comprises two pockets, one of which is located on each side of the transverse centerline, with a "wing" (the central component of the side wrapping element) positioned between the pockets. The wing is free to pivot longitudinally, while still remaining between the pockets. The wing has indentations 62 on either end (that is, the transverse end portion 60 of the central component has indentations or notches 62) to facilitate this pivoting action and to reduce the stress associated with wrapping the side wrapping elements around the panty. The pockets prevent liquids from wicking around or between the wing. In other words, the central component 50A has a proximal edge adjacent the main body portion, a distal edge spaced away from the main body portion, and a smaller dimension measured in the longitudinal direction at its proximal edge than at its distal edge.

Figure 5:
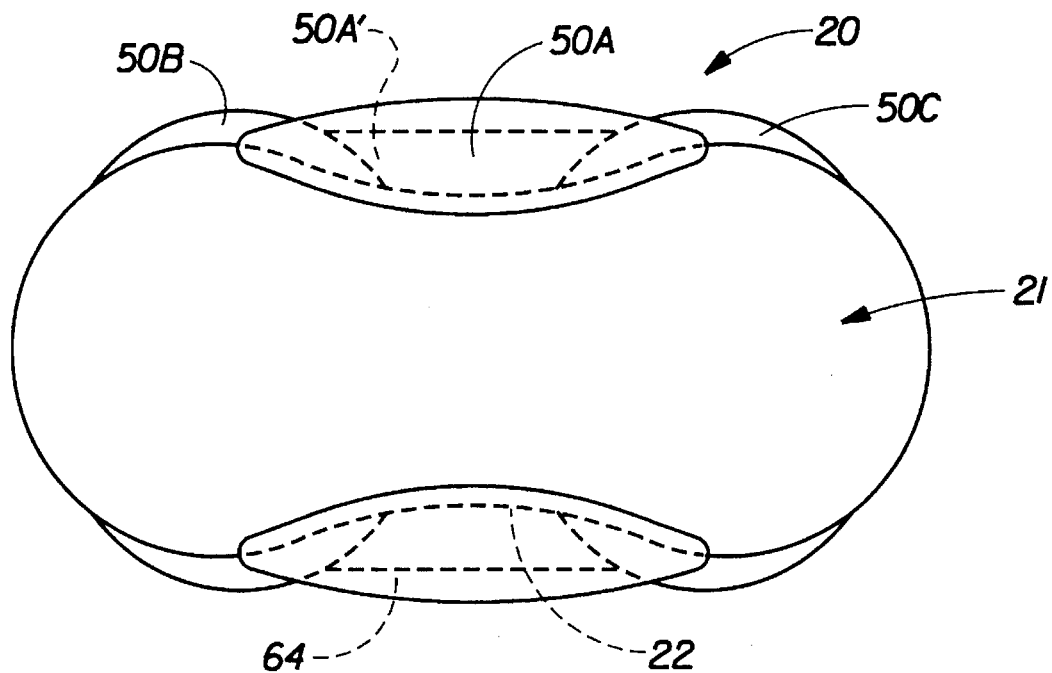
FIG. 5 is a top plan view of a sanitary napkin having an alternative arrangement of side wrapping element components.

FIG. 5 shows a sanitary napkin having side wrapping element components in an alternative arrangement. In the embodiment shown in FIG. 5, instead of the central component 50A being integral with the main body portion, the end components 50B and 50C are integral extensions of a component or components of the main body portion (such as the backsheet). In this embodiment, the central components 50A and 50A' comprise separate pieces that are attached to the main body portion 21 of the sanitary napkin. This alternative arrangement has the advantage of being somewhat simpler to make than the embodiment shown in FIGS. 1–3. The embodiment shown in FIG. 5 only requires that two separate elements (50A and 50A') be attached to the main body portion to form each side wrapping element 52, versus four elements in the embodiment shown in FIGS. 1–3.

Figure 6:
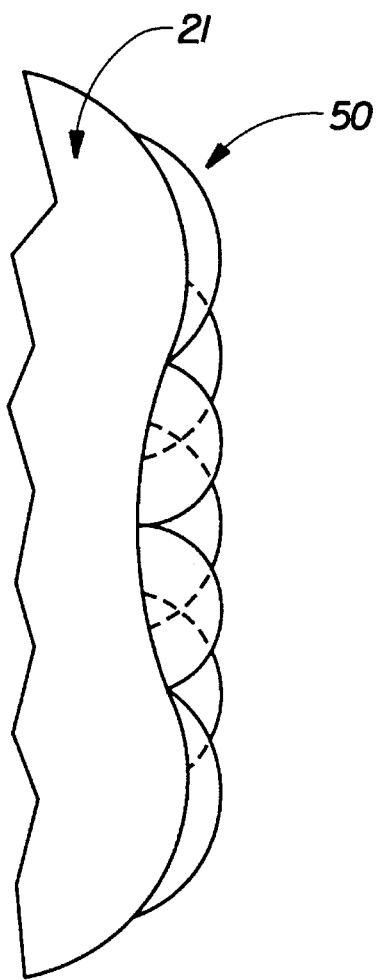
FIGS. 6 and 7 are plan views of portions of a sanitary napkin having side wrapping elements with different configurations.
Figure 7:
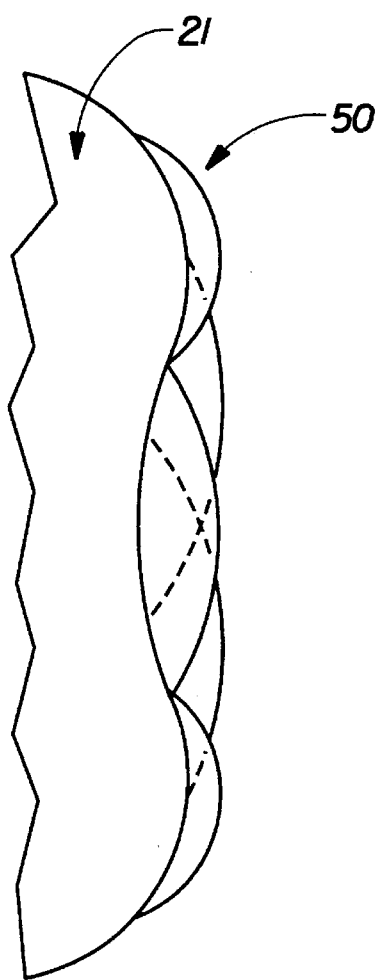

FIGS. 6 and 7 show portions of a sanitary napkin having side wrapping elements in other alternative configurations. The components of the side wrapping elements 50 shown in FIGS. 6 and 7 overlap in ways which do not necessarily form the "pocket door" structure shown in FIGS. 1–3. The structure of the components of the side wrapping elements shown in FIGS. 6 and 7 is intended to function like the shell of an armadillo in the way the components can spread apart but still overlap.

In other alternative embodiments, the side wrapping elements 50 may be integral portions of one or more components of the main body portion. In addition, while the side wrapping elements 50 are shown as extending from each longitudinal edge of the main body portion, there may only be one side wrapping element extending from one of the edges of the main body portion. Further, the side wrapping elements are preferably mirror images of each other, and are symmetrical about the longitudinal centerline. However, it should be understood that the shape and location of the side wrapping elements described herein are those of a preferred embodiment, and other embodiments are also possible. For instance, the side wrapping elements 50 may be offset along the longitudinal centerline more towards one end edge of the main body portion than the other.

In still other embodiments, the side wrapping element components may be separate elements that are joined underneath to the main body portion 21 of the sanitary napkin inboard of the longitudinal side edges 22 of the main body portion. The side wrapping elements 50, in such a case, are preferably otherwise unattached to the garment-facing side of the main body portion 21 of the sanitary napkin 20 between the points of attachment and the longitudinal side edges 22 of the main body portion. This allows the side wrapping elements 50 to fit a broader range of panty styles and sizes.

The terms "panty liner" or "pantiliner" refer to absorbent articles that are less bulky than sanitary napkins which are generally worn by women between their menstrual periods. Suitable absorbent articles in the form of pantiliners that can be provided with the side wrapping elements described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the side wrapping elements described herein are disclosed in U.S. Pat. No. 5,300,054 issued to Feist, et al. on Apr. 5, 1994 and U.S. Pat. No. 5,304,161 issued to Noel, et al. Apr. 19, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent article having a longitudinal dimension extending in a longitudinal direction and a transverse dimension extending in a transverse direction, said absorbent article comprising:

a main body portion comprising an absorbent core, said main body portion having a body-facing side, a garment-facing side, and a pair of longitudinal side edges; and a pair of side wrapping elements joined to said main body portion and extending laterally outward beyond the longitudinal side edges of said main body portion to distal edges, wherein at least one of said side wrapping elements comprises more than one side wrapping element component, said side wrapping element components being flexible and joined to said main body portion at a proximal edge so that they are at least partially overlapping and unattached to each other along at least a portion of the distal edge of said side wrapping element so that the portions of said side wrapping element components comprising the distal edge of said side wrapping element are free to move relative to each other and spread apart when said side wrapping elements are folded.

2. The absorbent article of claim 1 wherein said main body portion comprises a first end region, a second end region, and a central region disposed between said end regions, and said at least one side wrapping element comprises a central component extending outward beyond a longitudinal side edge of said main body portion in said central region of said absorbent article and two end components, one end component extending outward beyond said longitudinal side edge in each of said end regions of said absorbent article so that it overlaps at least a portion of said central component.

3. The absorbent article of claim 2 wherein said central component has a body-facing side and a garment-facing side and said side wrapping element comprises two end components in each end region of said absorbent article and one end component is disposed over at least a portion of the body-facing side of the central component and the second end component is disposed over at least a portion of the garment-facing side of the central component in each end region of said absorbent article.

4. The absorbent article of claim 3 wherein said central component has a proximal edge adjacent said main body portion and a distal edge, and said central component has a smaller dimension measured in the longitudinal direction at its proximal edge than at its distal edge.

5. The absorbent article of claim 4 wherein said central component has two transverse end portions and said two end components in each end region of said absorbent article are joined together outboard of the transverse end portions of said central component with a liquid impervious seal so that at least a portion of said central component is covered on its body-facing side and its garment-facing side by portions of said end components and said liquid impervious seal closes off portions of said end components to form a pocket for said central component.

6. The absorbent article of claim 1 wherein said main body portion comprises a first end region, a second end region, and a central region disposed between said end regions, and said at least one side wrapping element comprises two central components extending outward beyond a longitudinal side edge of said main body portion in said central region of said absorbent article and two end components, one end component extending outward beyond said longitudinal side edge in each of said end regions of said absorbent article, wherein said central components are joined to said main body portion so that they extend over an cover a part of said end components to overlap at least a portion of said end components.

7. The absorbent article of claim 6 wherein one central component is joined the body-facing side of said main body portion so that it extends over at least a portion of the body-facing side of both of said end components and the second central component is disposed to overlap at least a portion of the garment-facing side of both of said end components.

8. The absorbent article of claim 7 wherein said central components each have a distal edge and said end components each have a distal edge, and said central components overlap a portion of the distal edges of said end components, and said two central components are joined together outboard of the portions of said end components that are overlapped by said central components, and said central component with a liquid impervious seal so that at least a portion of said end components are covered on their body-facing side and their garment-facing side by portions of said central components and said liquid impervious seal closes off portions of said central components to form pockets for said end components.

* * * * *